United States Patent
Palaniappan et al.

(10) Patent No.: US 6,982,345 B2
(45) Date of Patent: Jan. 3, 2006

(54) PROCESS FOR PREPARATION OF CINNAMATES USING POLYANILINE SALTS AS CATALYSTS

(75) Inventors: Srinivasan Palaniappan, Andra Pradesh (IN); Malladi Sairam, Andra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 519 days.

(21) Appl. No.: 10/075,933

(22) Filed: Feb. 13, 2002

(65) Prior Publication Data

US 2004/0049068 A1 Mar. 11, 2004

(51) Int. Cl.
*C07C 69/74* (2006.01)
(52) U.S. Cl. ...................................................... 560/128
(58) Field of Classification Search ................. 560/128
See application file for complete search history.

(56) References Cited

FOREIGN PATENT DOCUMENTS

JP 04-077455 * 11/1992

* cited by examiner

Primary Examiner—Cecilia J. Tsang
Assistant Examiner—Taylor Victor Oh
(74) *Attorney, Agent, or Firm*—Abelman, Frayne & Schwab

(57) ABSTRACT

The present invention relates to a process for preparation of cinnamates using polyaniline salts as catalysts. The present invention more particularly relates to a process for producing cinnamic esters by the direct esterification of cinnamic acid with aliphatic alcohols over polyaniline salts as catalysts.

The process of esterification may be carried out by reacting cinnamic acid with aliphatic mono hydric alcohol in presence of catalyst, removing the catalyst by conventional methods. The ester can be isolated such as filtration followed by isolation of esters by conventional column chromatography using adsorbent such as silica gel and solvent such as chloroform, ethylacetate, hexane and mixture there off.

16 Claims, No Drawings

PROCESS FOR PREPARATION OF CINNAMATES USING POLYANILINE SALTS AS CATALYSTS

The present invention relates to a process for preparation of cinnamates using polyaniline salts as catalysts. The present invention more particularly relates to a process for producing cinnamic esters by the direct esterification of cinnamic acid with aliphatic alcohols over polyaniline salts as catalysts.

Cinnamic acid esters are used in flavor, fragrance compositions created for products which include soaps and cosmetics as well as beverages, backed goods and convenience foods.

Esterification is a well known equilibrium limited reaction involving reaction of a mono-, di- or polycarboxylic acid (or, in suitable cases, an acid anhydride) with an alcohol or phenol component. Such an alcohol or phenol component can be mono, di- or polyhydric.

Several synthetic routes exist to make esters, but most of them are not suitable to meet the stringent specifications which are being applied in the chemical industry. The most acceptable method of making an ester is to react an acid with an alcohol in the presence of catalyst.

Esterification is one of the most fundamental and important reactions in organic synthesis. Conventionally, the processes of making esters from acids and alcohols can be classified into the following three main categories: (R. C. Larock, Comprehensive Organic Transformations, VCH, New York, 1989, page 966, references therein; Encyclopedia of Chemical Technology, Vol 9, $4^{th}$ Edition, Wiley Interscience Publications, Page 755, references therein; Ullmann's Encyclopedia of Industrial Chemistry, Vol.10, Vth Edition, 1987, Page 281, references therein; Vogel's, Text book of Practical Organic Chemistry, Longman Group Ltd., England, Vth Edition, 1996).

(a) Liquid-phase esterification reaction utilizing a liquid catalyst: This type of processes utilize liquid phase acid, such as sulfuric acid, phosphoric acid, sulfonic acid, or p-toluene sulfonic acid, as catalysts.

(b) Liquid phase esterification reaction utilizing a solid catalyst: This type of processes typically utilize inorganic salts, cationic ionic exchange resin and solid acid catalyst etc.

(c) Gas phase esterification reaction: This type of processes utilize a variety of catalysts such as heteropolyacids, liquid phase acids carried by a solid carrier, and zeolite in a gas phase reaction.

One of the problems associated with the liquid-catalyst liquid-phase esterification reaction is that the acidic liquid catalysts of sulfuric acid or p-toluene sulfonic acid can cause corrosion problems to the reactor. These liquid acid catalysts are also discharged along with the reaction products, thus causing severe waste disposal and pollution problems. The drawbacks of using mineral acid as catalyst are: (i)Catalyst can not be reused, (ii) Disposal of acid is not environmentally safe and it is not economical, (iii) Low selectivity is frequently observed, (iv) Corrosion of the reaction vessel and reactors, (v) Not easy to handle and (iv) High inventory of the catalyst.

The solid-catalyst, liquid-phase esterification reaction, which typically utilizes a cationic ionic exchange resin as catalyst, ameliorates the corrosion and waste disposal problems experienced with the liquid-catalyst liquid-phase processes, and results in simplified separation procedure required between the reaction product and catalysts. However, cationic ion-exchange resins typically exhibit relatively poor heat-resistance, and they often lose substantial activity after being subject to heat. Once the catalytic activity of the cationic ion-exchange resins is reduced, it is difficult to be regenerated.

In the gas phase esterification reaction, the reaction conditions are maintained so that all the reactants and products are in the gas phase. Typically, inorganic materials are utilized as catalysts which typically exhibit excellent heat resistance and can be easily separated from the reaction products. However, the gas phase reaction necessitates a relatively large reaction vessel, resulting in large capital investment cost. Furthermore, if the gas phase esterification reaction is utilized to produce unsaturated carboxylic esters, the high reaction temperature often causes undesired by-products of polymers or oligomers to be produced. In certain instances, the high reaction temperature has caused the alcohol molecules to be dehydrated to become ethers. These side-reactions will tend to cause the reaction catalysts to lose their activity and result in operational difficulties.

The main object of the present is to provide a process for preparation of cinnamates using polyaniline salts as catalysts which obviates the drawbacks as detailed above.

Another object of the present invention is to produce cinnamic esters by the direct esterification of cinnamic acid with aliphatic monohydric alcohols over polyaniline salt as catalyst.

Accordingly, the present invention relates to a process for preparation of cinnamates using polyaniline salt as catalyst, which comprises esterifying cinnamic acid directly with an aliphatic mono hydric alcohol in the presence of polyaniline salt as catalyst at a temperature ranging between 30 to 80° C. for a period ranging from 4 to 24 hrs., removing the catalyst from the reaction mixture and separating the desired ester by conventional method.

In an embodiment of the present invention the aliphatic mono hydric alcohol used is selected from the group consisting of methyl alcohol, ethyl alcohol, propyl alcohol and butyl alcohol.

In an another embodiment the catalyst used is a polyaniline salt selected from the group consisting of polyaniline-sulfuric acid, polyaniline-hydrochloric acid, and polyaniline-nitric acid systems.

In yet another embodiment the reaction is carried out at a temperature preferably in the range of 70 to 80° C.

In yet another embodiment the reaction is carried out for a period preferably in the range of 20 to 24 hrs.

In still another embodiment the catalyst used is recyclable for at least six times.

The process of esterification may be carried out by reacting cinnamic acid with aliphatic mono hydric alcohol in presence of catalyst, removing the catalyst by conventional methods. The ester can be isolated such as filtration followed by isolation of esters by conventional column chromatography using adsorbent such as silica gel and solvent such as chloroform, ethylacetate, hexane and mixture there off.

The following examples are given by way of illustration and therefore should not be construed as limit the scope of the present invention.

EXAMPLE 1

Two different methods were used to prepare polyaniline salts using two different oxidizing agents such as benzoyl peroxide and ammonium persulfate.

Method 1: Preparation of Polyaniline Salts Using Benzoyl Peroxide

In the polymerization process, 25 ml aqueous solution containing 1.44 g of sodium lauryl sulfate was added slowly while stirring to the solution of 150 ml acetone containing 4.85 g benzoyl peroxide. In to this mixture, 30 ml aqueous solution containing 2.4 ml of aniline and 9 ml of concentrated sulfuric acid was added under constant stirring. The reaction mixture was stirred for 24 hrs at 30° C. The reaction mixture was filtered, washed with water and finally with acetone. The sample was dried at 100° C. till a constant weight. Using the same procedure, polyaniline salts were prepared using 9 ml hydrochloric acid and 6 ml nitric acid respectively instead of sulfuric acid.

Method 2: Preparation of Polyaniline Salts Using Ammonium Persulfate

In polymerization process, 1.0 ml of aniline and 3.0 ml of concentrated sulfuric acid were dissolved in 70 ml distilled water. To this solution, 25 ml aqueous solution containing 2.3 g of ammonium persulfate was added dropwise (15–20 min. interval). The reaction mixture was stirred for 4 hrs. at 30° C. The reaction mixture was filtered, washed with water and finally with acetone. The sample was dried at 100° C. till a constant weight. Using the same procedure, polyaniline salts were prepared using 9 ml hydrochloric, 6 ml nitric acid respectively instead of sulfuric acid.

EXAMPLE 2

In a typical experiment, 1.0 g of cinnamic acid was taken in 10 ml round bottom flask and added 5.0 ml of methanol and 200 mg of catalyst powder (method 1—polyaniline-sulfate salt). The reaction mixture was refluxed at 7020 C. for different intervals of time. Filtered the reaction mixture and used chloroform to wash the mixture to recover the catalyst. Evaporated the chloroform solvent and unreacted methanol. Loaded the compound in a column containing silica gel of finer than 200 mesh. The product is eluted with 20:80 chloroform and hexane mixture using 400 ml volume. The solvent mixture were recovered to get the pure ester.

The yield of the ester prepared with different reaction time are given in

| REACTION TIME (hrs.) | YIELD (%) |
| --- | --- |
| 4 | 39 |
| 8 | 63 |
| 12 | 78 |
| 20 | 82 |
| 24 | 99 |

EXAMPLE 3

In a typical experiment, 1.0 g of cinnamic acid was taken in 10 ml round bottom flask and added 5.0 ml of methanol and different amount of catalyst powder (method 1—polyaniline-sulfate salt). The reaction mixture was refluxed at 70° C. for 24 hrs. Filtered the reaction mixture and used chloroform to wash the mixture to recover the catalyst. Evaporated the chloroform solvent and unreacted methanol. Loaded the compound in a column containing silica gel of finer than 200 mesh. The product is eluted with 20:80 chloroform and hexane mixture using 400 ml volume. The solvent mixture were recovered to get the pure ester.

The yield of the ester prepared with different amount of catalyst are given in Table 3.

| AMOUNT OF CATALYST (mg.) | YIELD (%) |
| --- | --- |
| 50 | 52 |
| 100 | 72 |
| 150 | 80 |
| 200 | 99 |

EXAMPLE 4

In a typical experiment, 1.0 g of cinnamic acid was taken in 10 ml round bottom flask and added various amount of methanol and 200 mg of catalyst powder (method 1—polyaniline-sulfate salt). The reaction mixture was refluxed at 70° C. for 24 hrs. Filtered the reaction mixture and used chloroform to wash the mixture to recover the catalyst. Evaporated the chloroform solvent and unreacted methanol. Loaded the compound in a column containing silica gel of finer than 200 mesh. The product is eluted with 20:80 chloroform and hexane mixture using 400 ml volume. The solvent mixture were recovered to get the pure ester.

The yield of the ester prepared with different amount of methanol are given in Table4.

| AMOUNT OF METHANOL (ml) | YIELD (%) |
| --- | --- |
| 3 | 45 |
| 4 | 82 |
| 5 | 99 |

EXAMPLE 5

In a typical experiment, 1.0 g of cinnamic acid was taken in 10 ml round bottom flask and added 5.0 ml of methanol and 200 mg of catalyst powder (method 1—polyaniline-sulfate salt). The reaction mixture was refluxed at different temperatures for 24 hrs. Filtered the reaction mixture and used chloroform to wash the mixture to recover the catalyst. Evaporated the chloroform solvent and unreacted methanol. Loaded the compound in a column containing silica gel of finer than 200 mesh. The product is eluted with 20:80 chloroform and hexane mixture using 400 ml volume. The solvent mixture were recovered to get the pure ester.

The yield of the ester prepared with different temperatures are given in

| TEMPERATURE (° C.) | YIELD (%) |
| --- | --- |
| 30 | 28 |
| 50 | 60 |
| 70 | 99 |

EXAMPLE 6

In a typical experiment, 1.0 g of cinnamic acid was taken in 10 ml round bottom flask and added 5.0 ml of alcohol (different alcohols) and 200 mg of catalyst powder (method 1—polyaniline-sulfate salt). The reaction mixture was refluxed for 24 hrs. Filtered the reaction mixture and used chloroform to wash the mixture to recover the catalyst. Evaporated the chloroform solvent and unreacted methanol. Loaded the compound in a column containing silica gel of finer than 200 mesh. The product is eluted with 1:99 ethyl acetate and hexane mixture using 400 ml volume. The solvent mixture were recovered to get the pure ester.

The yield of the ester prepared with different alcohols are given in Table 6.

| ALCOHOL | YIELD (%) |
| --- | --- |
| Methanol | 99 |
| Ethanol | 95 |
| Propanol | 48 |
| Butanol | 91 |
| Myristyl alcohol | 16 |
| Behnyl alcohol | 14 |
| Iso propyl alcohol | 9 |
| Tertiary butyl alcohol | 5 |

EXAMPLE 7

In a typical experiment, 1.0 g of cinnamic acid was taken in 10 ml round bottom flask and added 5.0 ml of methanol and 200 mg of catalyst powder (method 1—polyaniline-sulfate salt). The reaction mixture was refluxed at 70° C. for 24 hrs. Filtered the reaction mixture and used chloroform to wash the mixture to recover the catalyst. Evaporated the chloroform solvent and unreacted methanol. Loaded the compound in a column containing silica gel of finer than 200 mesh. The product is eluted with 20:80 chloroform and hexane mixture using 400 ml volume. The solvent mixture were recovered to get the pure ester. The experiment was carried out six times using the recovered catalyst.

The yield of the ester prepared with recovered catalyst are given in Table7.

| REPEATABILITY (no of times) | YIELD (%) |
| --- | --- |
| First | 99 |
| Second | 99 |
| Third | 99 |
| Fourth | 99 |
| Fifth | 99 |
| Sixth | 99 |
| Seventh | 99 |

EXAMPLE 8

In a typical experiment, 1.0 g of cinnamic acid was taken in 10 ml round bottom flask and added 5.0 ml of methanol and 200 mg of catalyst powder (prepared by two different methods). The reaction mixture was refluxed at 70° C. for 24 hrs. Filtered the reaction mixture and used chloroform to wash the mixture to recover the catalyst. Evaporated the chloroform solvent and unreacted methanol. Loaded the compound in a column containing silica gel of finer than 200 mesh. The product is eluted with 20:80 chloroform and hexane mixture using 400 ml volume. The solvent mixture were recovered to get the pure ester.

The yield of the ester prepared with different catalyst are given in Table 8.

| METHOD | POLYANILINE SALT | YIELD (%) |
| --- | --- | --- |
| I | Polyaniline hydrochloric acid system | 50 |
|  | Polyaniline sulfuric acid system | 99 |
|  | Polyaniline nitric acid system | 60 |
| II | Polyaniline hydrochloric acid system | 41 |
|  | Polyaniline sulfuric acid system | 99 |
|  | Polyaniline nitric acid system | 58 |

The main advantages of the present invention are: the use of polyaniline-salts as catalysts in the liquid phase esterification of aliphatic mono carboxylic acids with aliphatic mono hydric alcohols for the first time. Also, the use of polyaniline salts as catalysts provides the following advantages compared with the use of other catalysts
  (i) repeated use of catalyst is possible.
  (ii) allowing recycling of catalyst.
  (iii) separation of catalyst from a reaction mixture is easy
  (iv) catalyst do not corrode the reaction vessel or reactor
  (v) there is no problem for the disposal of used catalyst as they are environmentally safe, though the disposal of mineral acid catalyst requires much money for treatment to make it environmentally safe.
  (vi) the catalyst is economical and (vii) the preparation of the catalyst is very easy.

In view of the above, it will be seen that several advantages of the invention are achieved and other advantageous results attained. As various changes could be made in the above methods and compositions without departing from the scope of the invention, it is intended that all matter contained in the above description shall be interpreted as illustrative and not in a limiting sense.

What is claimed is:

1. A process for preparation of cinnamates using polyaniline salt as catalyst, which comprises esterifying cinnamic acid directly with an aliphatic mono hydric alcohol in the presence of polyaniline salt as catalyst at a temperature ranging from about 30 to about 80° C. for a period ranging from about 4 to about 24 hours removing the catalyst from the reaction mixture and separating the desired ester by filtration.

2. The process as claimed in claim 1, wherein the aliphatic mono hydric alcohol used is selected from the group consisting of methyl alcohol, ethyl alcohol, propyl alcohol, and butyl alcohol.

3. The process as claimed in claim 1, wherein the catalyst used is a polyaniline salt selected from the group consisting of polyaniline-sulfuric acid, polyaniline-hydrochloric acid, and polyaniline-nitric acid systems.

4. The process as claimed in claim 1, wherein the reaction is carried out at a temperature in the range of about 70 to about 80° C.

5. The process as claimed in claim 1, wherein the reaction is carried out for a period of about 20 to about 24 hours.

6. The process as claimed in claim 1, wherein the catalyst used is recyclable for at least six times.

7. The process as claimed in claim 2, wherein the catalyst used is a polyaniline salt selected from the group consisting of polyaniline-sulfuric acid, polyaniline-hydrochloric acid, and polyaniline-nitric acid systems.

8. The process as claimed in claim 2, wherein the reaction is carried out at a temperature in the range of 70 to 80° C.

9. The process as claimed in claim 3, wherein the reaction is carried out at a temperature in the range of 70 to 80° C.

10. The process as claimed in claim 2, wherein the reaction is carried out for a period of 20 to 24 hours.

11. The process as claimed in claim 3, wherein the reaction is carried out for a period of 20 to 24 hours.

12. The process as claimed in claim 4, wherein the reaction is carried out for a period of 20 to 24 hours.

13. The process as claimed in claim 2, wherein the catalyst used is recyclable for at least six times.

14. A process as claimed in claim 3, wherein the catalyst used is recyclable for at least six times.

15. The process as claimed in claim 4, wherein the catalyst used is recyclable for at least six times.

16. The process as claimed in claim 5, wherein the catalyst used is recyclable for at least six times.

* * * * *